(12) United States Patent
Canavan

(10) Patent No.: US 7,003,811 B2
(45) Date of Patent: Feb. 28, 2006

(54) DETACHABLE AND ROTATABLE CLIP

(75) Inventor: Richard W. Canavan, Woodstock, CT (US)

(73) Assignee: Bacou-Dalloz Eye & Face Protection, Inc., Smithfield, RI (US)

( * ) Notice: Subject to any disclaimer, the term of this patent is extended or adjusted under 35 U.S.C. 154(b) by 235 days.

(21) Appl. No.: 10/726,847

(22) Filed: Dec. 3, 2003

(65) Prior Publication Data
US 2005/0132478 A1 Jun. 23, 2005

(51) Int. Cl.
A61F 9/02 (2006.01)
(52) U.S. Cl. .......................................... 2/448
(58) Field of Classification Search .................... 2/441, 2/448, 452; 351/43
See application file for complete search history.

(56) References Cited

U.S. PATENT DOCUMENTS

| 1,554,448 | A |   | 9/1925 | McKnight et al. |
| 3,096,553 | A |   | 7/1963 | Gould |
| 3,373,444 | A |   | 3/1968 | Militello |
| 4,559,678 | A |   | 12/1985 | Birkenstock |
| 4,924,557 | A |   | 5/1990 | Heckerman et al. |
| 4,976,531 | A |   | 12/1990 | Kahaney |
| 5,002,381 | A |   | 3/1991 | Murrell |
| 5,189,447 | A | * | 2/1993 | Oleson ....................... 351/121 |
| 5,410,763 | A |   | 5/1995 | Bolle |
| 5,659,381 | A |   | 8/1997 | Simioni |
| 5,706,527 | A |   | 1/1998 | Kita et al. |
| 5,768,716 | A | * | 6/1998 | Porsche ......................... 2/454 |
| 5,845,341 | A |   | 12/1998 | Barthold et al. |
| 6,024,446 | A | * | 2/2000 | Hall et al. ................... 351/120 |
| 6,149,268 | A |   | 11/2000 | Hall et al. |
| 6,276,794 | B1 |  | 8/2001 | Chiang |
| 6,349,420 | B1 |  | 2/2002 | Chiang |
| 6,477,717 | B1 |  | 11/2002 | Wineforder et al. |

* cited by examiner

Primary Examiner—Katherine M. Moran
(74) Attorney, Agent, or Firm—Salter & Michaelson

(57) ABSTRACT

A clip for attaching a strap to a pair of eye wear, such as goggles, includes a body portion, a slot to secure an end of the strap, a detent supported on the body to rotatably secure the clip to the goggle, and an engagement member for removably attaching the clip to the goggle. In one embodiment, the engagement member is a pivotal fastener that is movable between a position where the clip is attached to the goggle body and a position where it is removed from the goggle.

12 Claims, 7 Drawing Sheets

DETACHABLE AND ROTATABLE CLIP

TECHNICAL FIELD

The present disclosure is directed to a clip for securing a strap to eye wear, and more particularly, to a goggle clip which can be readily removed and rotated by the user.

BACKGROUND OF RELATED ART

Clips to secure a strap to eye wear, for example a pair of goggles, which are movable and detachable are known in the art. It is desirable that the clips securely attach the straps to the goggles, which are conventionally used for safety. It is also desirable that the goggle clips be readily adjustable and, if necessary, removable by the user. Because the user may be wearing gloves, or other protective wear, ease of moving and/or detaching the clips while wearing gloves is desirable. By being able to readily adjust the angle of the clips, the user can find a fit that is most comfortable for their particular needs. For example, if the user has braided hair, or a bun, the strap can be easily angled around the hair style by rotating the clips. In addition, if the strap breaks it is often easier to remove the clips and strap instead of repairing the strap.

U.S. Pat. No. 4,976,531 discloses an eyeglasses retainer strap having a connection member (27) including a slot (25) for receiving the strap (10), and a boss member (40) which extends outwardly from relieved side surface (33). The boss member (40) is receivable within aperture (43) of tubular sleeve member (42). The front end of the tubular sleeve member removably receives the ear retainer portion (18) of the temple members (16) of the glasses.

U.S. Pat. No. 5,410,763 discloses an eye shield which is held in place on the head of the user by a strap (13) attached to a rotatable connector (14), which is attached to a frame of the eye shield. The ability of the connector to rotate allows the position of the strap to be adjusted by the wearer. The connector includes a hub (70) and a tab (72), which is integrally connected to the hub by an arm (74). The connector also contains slots (76 and 78) through which strap (13) is inserted and affixed to the connector. The hub (70) is rotatably attached to the extension (24), thus allowing the strap (13) to be positioned at adjustable angles.

While various adjustable and removable clips for securing a strap to eye wear exist today, there is continued need in the art for improved clips that securely attach the strap while being easily adjustable and, if necessary, removable by the user.

SUMMARY

It is therefore an object of the clip disclosed herein to provide a clip that securely attaches a strap to eye wear, and which is also easily adjustable and removable by the user.

In a preferred embodiment, a pair of clips are provided to attach a strap to eye wear, for example a pair of goggles. Each clip includes a body portion, a slot to secure an end of the strap, a detent supported on the body to rotatably secure the clip to the goggle, and an engagement member for removably attaching the clip to the goggle. In one embodiment, the engagement member is a pivotal fastener that is movable between a position where the clip is attached to the goggle body and a position where it is removed from the goggle. In another embodiment, the clip may preferably be made of a plastic material and may be formed as a unitary member.

BRIEF DESCRIPTION OF THE DRAWINGS

It should be understood that the drawings are provided for the purpose of illustration only and are not intended to define the limits of the invention. The foregoing and other objects and advantages of the embodiments described herein will become apparent with reference to the following detailed description when taken in conjunction with the accompanying drawings in which.

DETAILED DESCRIPTION OF THE ILLUSTRATIVE EMBODIMENTS

Figure 1:
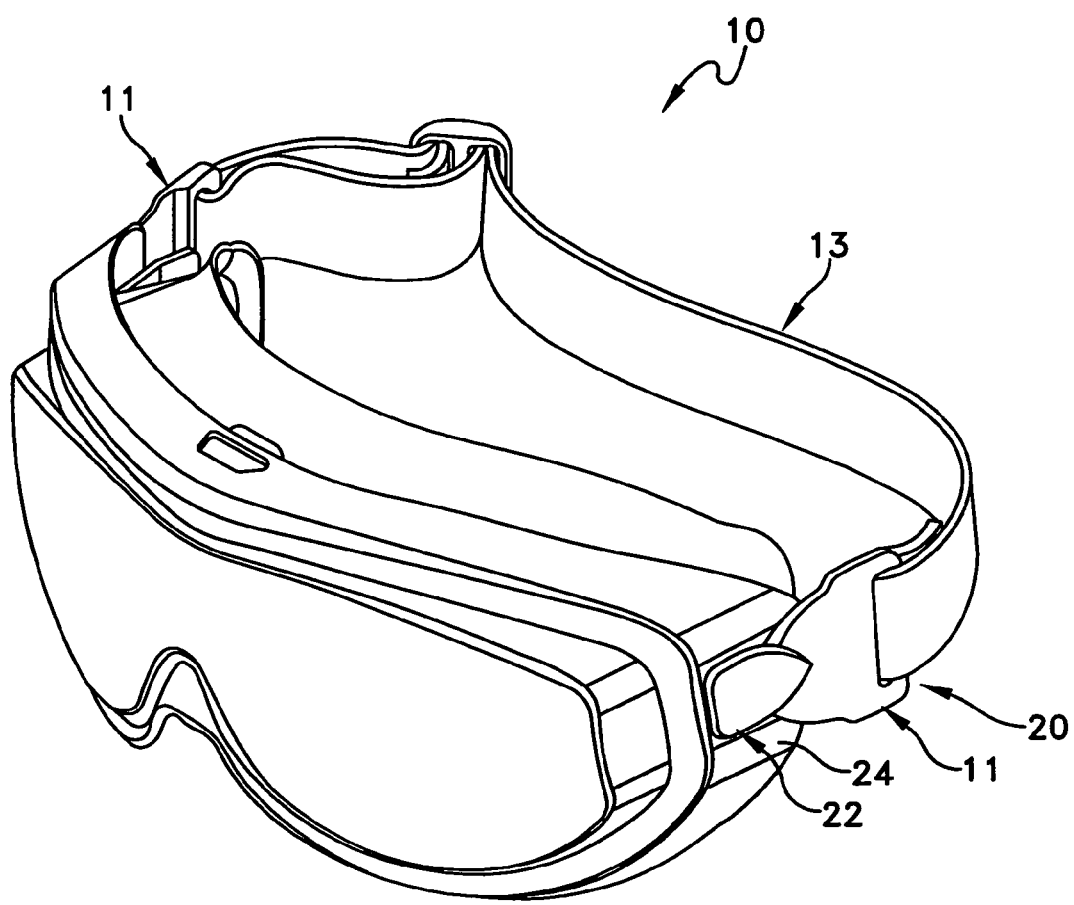
FIG. 1 is a perspective view of a goggle including a rotatable and removable clip for attaching a strap to the goggles.
Figure 2:
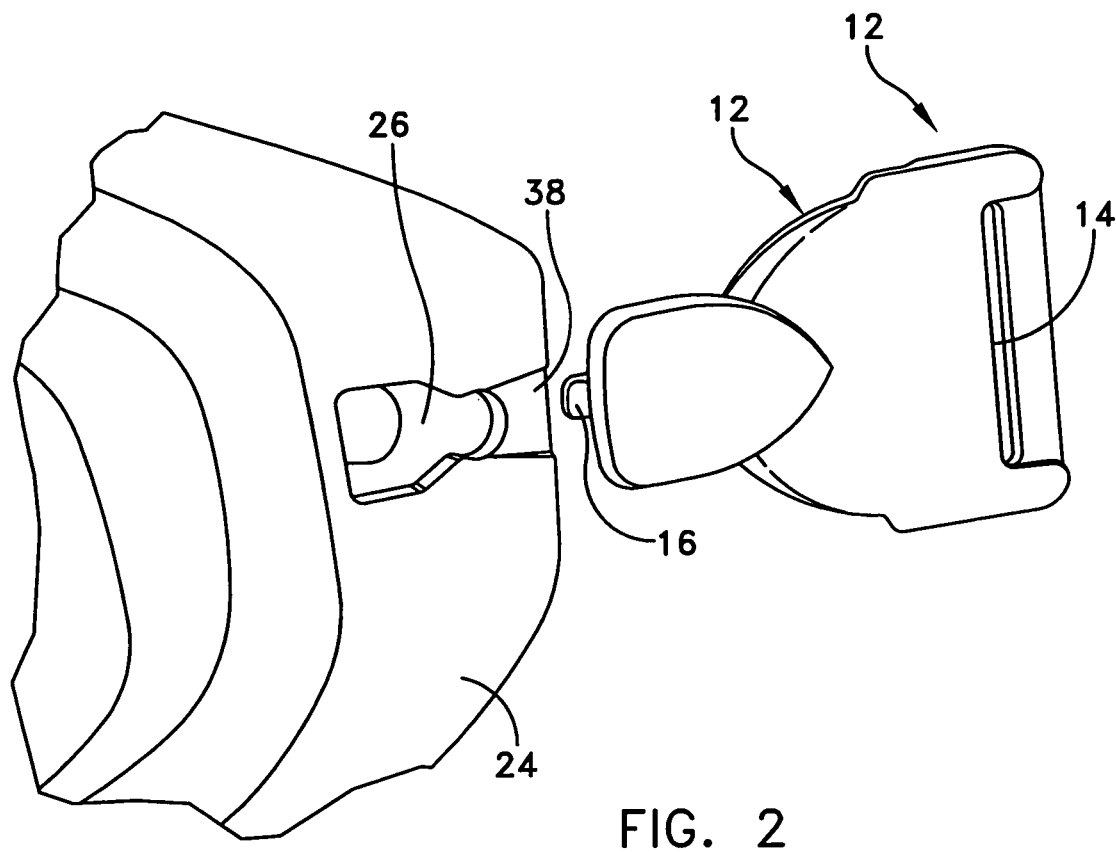
FIG. 2 is an exploded side view of the goggle clip of FIG. 1.
Figure 3:
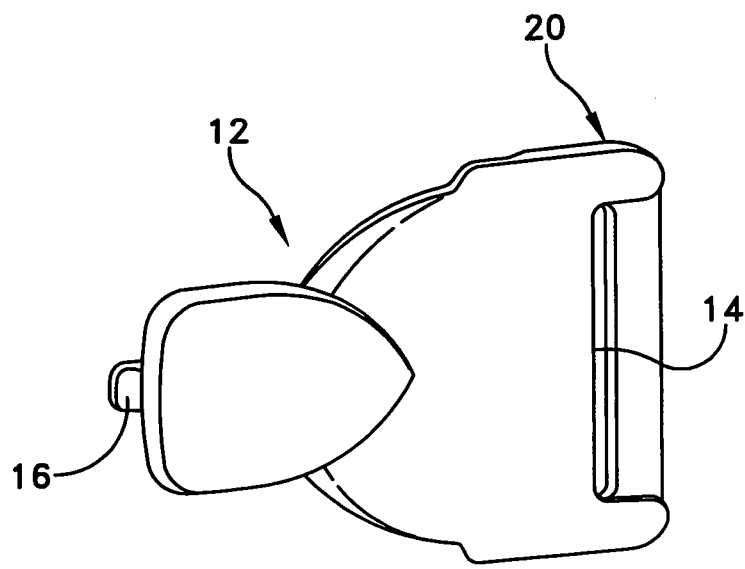
FIG. 3 is perspective view of the clip of FIG. 1.
Figure 4:
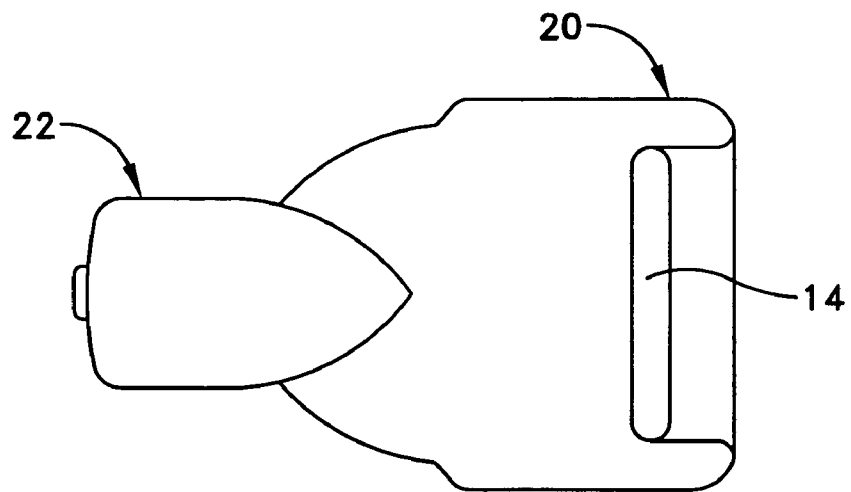
FIG. 4 is a top view of the clip of FIG. 1.
Figure 5:
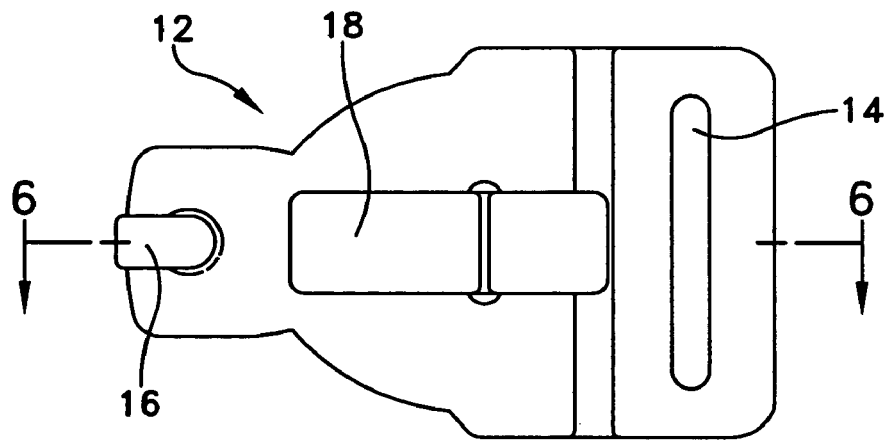
FIG. 5 is a bottom view of the clip of FIG. 1.
Figure 6:
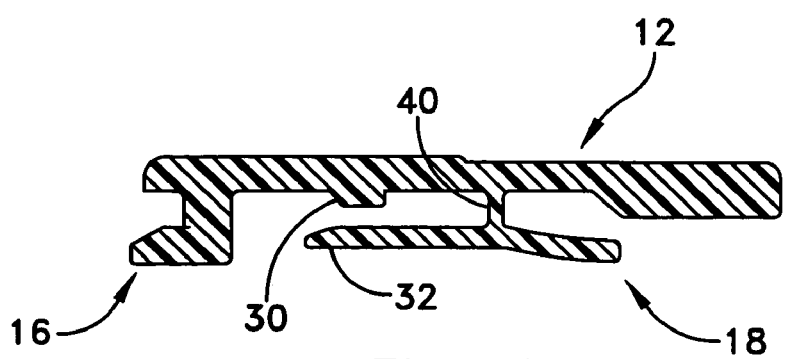
FIG. 6 is a cross sectional view taken along lines 6–6 of FIG. 5.
Figure 7:
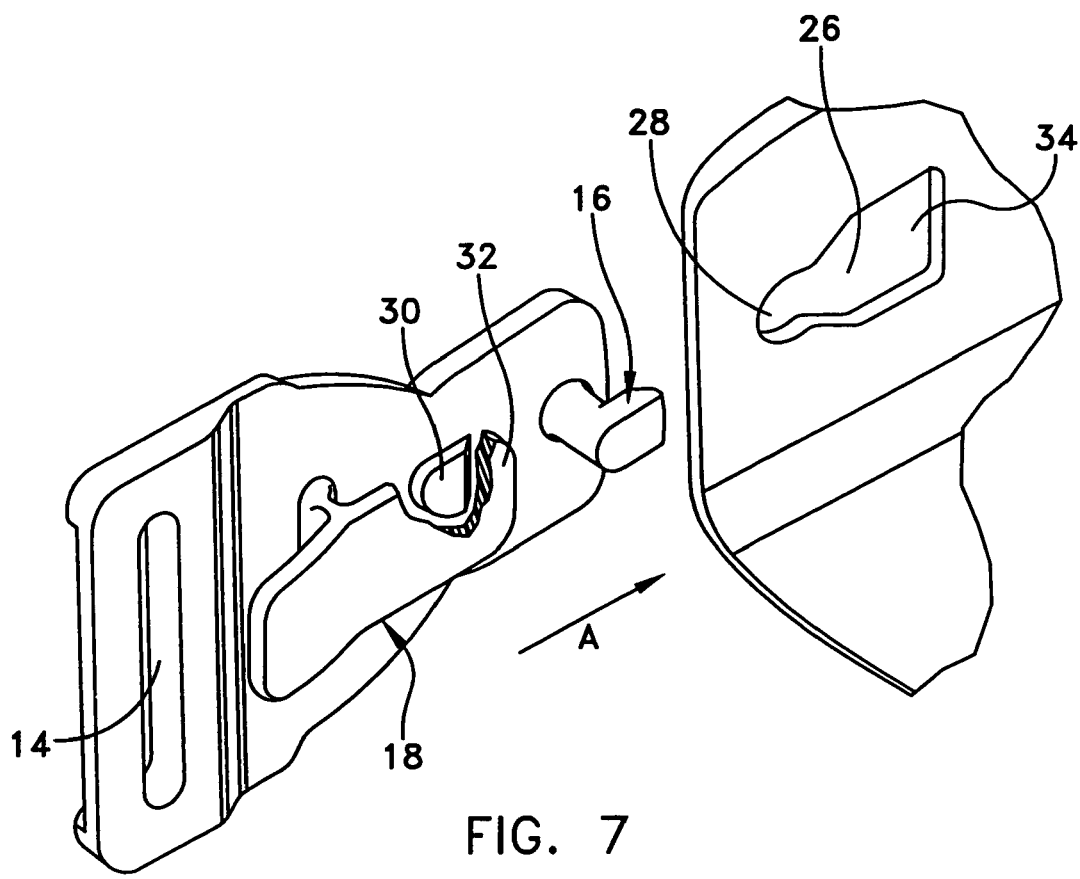
FIG. 7 is a partially broken away view of the clip of FIG. 1 before attachment to the goggles.
Figure 8:
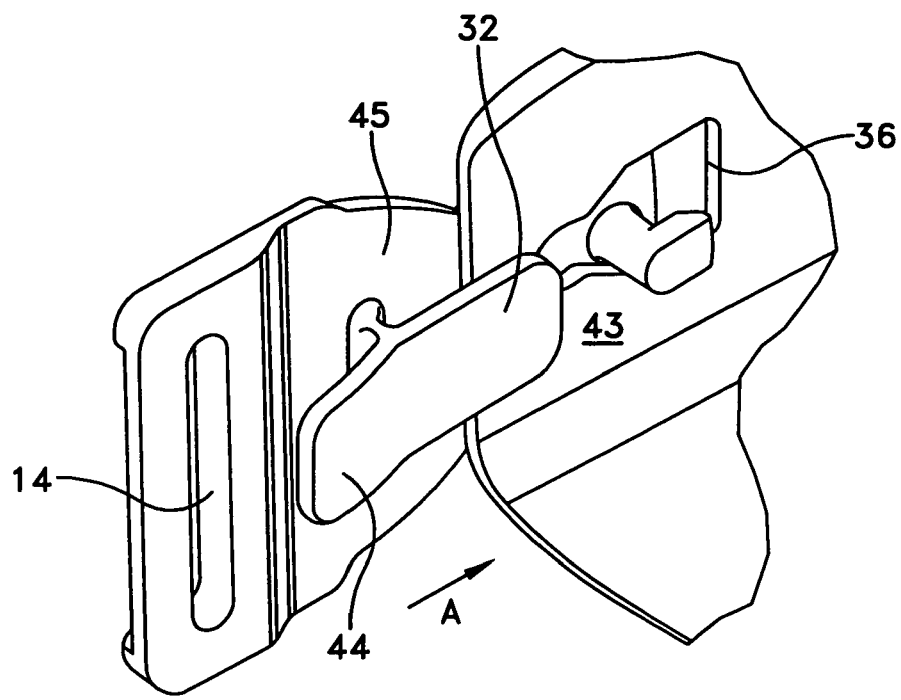
FIG. 8 is a rear, perspective view of the clip of FIG. 1 during insertion into the goggles.

A goggle 10 including a pair of clips 11 for attaching a strap 13 to eye wear is shown in FIGS. 1–13. As used herein, the term "eye wear" refers to any style or type of eye wear which can include a strap attached thereto. "Eye wear" is specifically not limited to goggles, or a particular style of goggles. The clips 11 each include a body portion 12 having a slot 14 at one end thereof, a detent 16 at an opposite end thereof, and an engagement member 18 disposed between the slot and the detent (FIG. 5). The body portion is preferably shaped such that the rear 20, which includes slot 14 is wider than the front 22, which supports the detent 16. In this manner, the front 22, which attaches to the side body 24 of the goggle is more compact and provides a less obtrusive connection. In the present embodiment, the body portion, detent and engagement member may preferably be formed of a plastic material, as a unitary member. Alternatively, the detent and engagement member may be formed as separate members, from a variety of materials, as would be known to those of skill in the art. The slot 14 in each clip is sized to receive one end of the strap 13 there through for attachment of the strap to the goggle 10 by the clips 11. A ramp 38 (FIG. 2) is preferably disposed on an outer surface of the side body 24 of the goggle, which aids in guiding the detent and engagement member into an opening 26, as described below.

Figure 9:
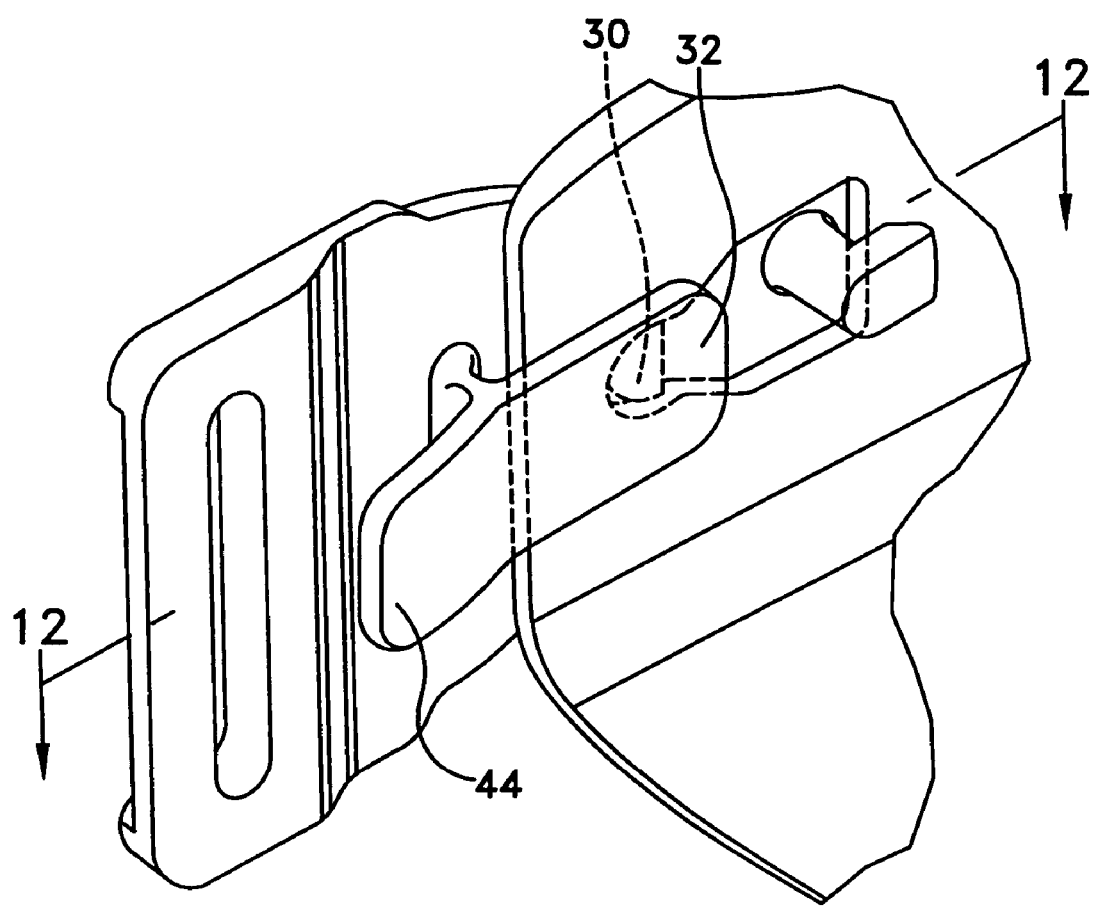
FIG. 9 is a rear, perspective view of the clip of FIG. 1 after insertion into the goggles.
Figure 13:
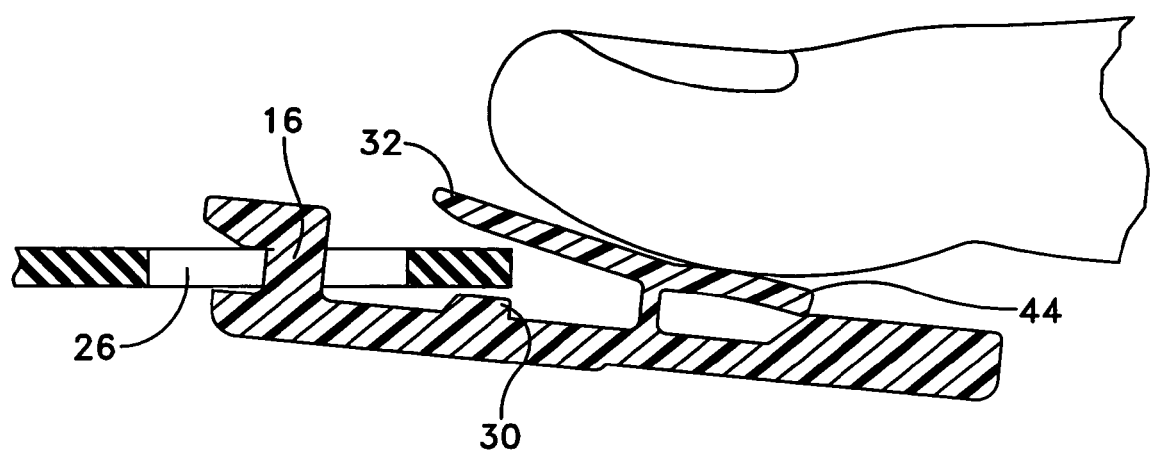
FIG. 13 is the cross sectional view of the clip shown in FIG. 12 being removed from the goggles.

In the present embodiment, engagement member 18 is a pivotal fastener including a post 40 which supports a lever 42 and which acts as a pivot point such that the clip is pivotable between a position where the clip is attached to the goggle body and a position where it is removable from the goggle body. In order to secure clip 11 to goggle body 24, the inner end 32 of the engagement member 18 is slid over the inside surface 43 of the goggle body 24, while the inner surface 45 of body portion 12 is slid over the ramp 38 in the direction of arrow "A", (FIG. 8), until stop 30 enters opening 28. Stop 30 is preferably supported on the inner surface 45 of the clip, opposite the inner end 32 of the engagement member. In the engaged, or attached position, the inner end 32 of the clip and stop 30 are in engagement with opening 28 such that the clip is secured to the goggle body (FIG. 9). In order to disengage the clip, a user pushes on the outer end 44 of the engagement member such that the outer end 44 is pushed downward, toward the clip body, and the inner end 32 is pivoted in an opposite direction, upward, away from the clip body (FIG. 13). Because the user simply pushes on the outer end of the clip, removal of the clip from the goggle can be easily achieved even when wearing protective equipment, for example gloves.

Figure 10:
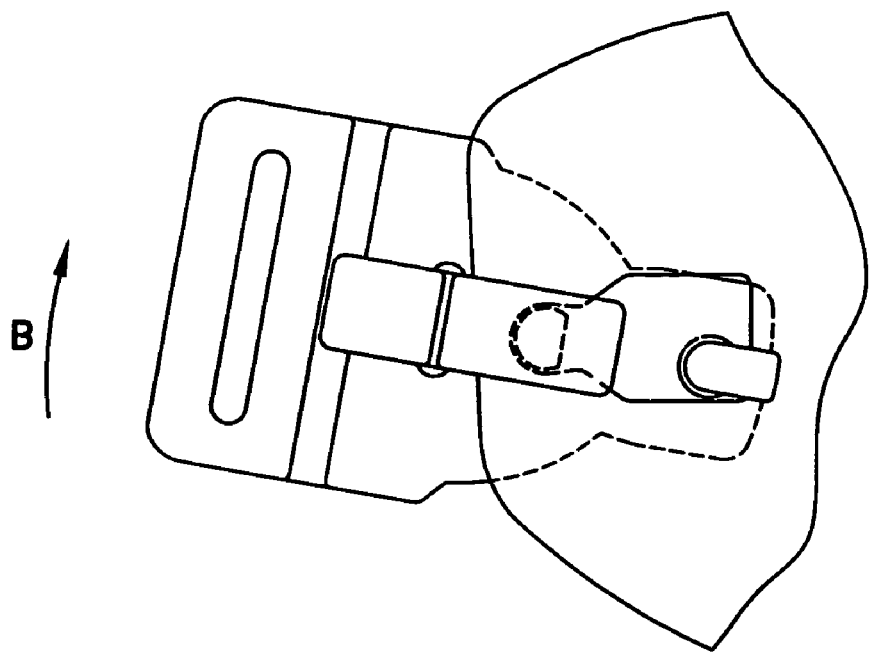
FIG. 10 is a rear, plan view of the clip of FIG. 9 rotated upward.
Figure 11:
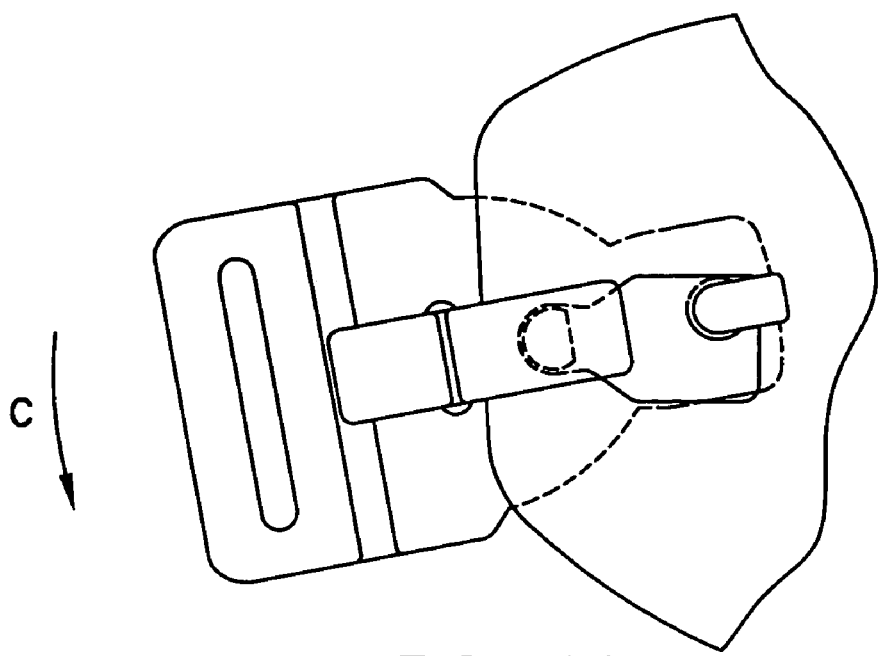
FIG. 11 is a rear, plan view of the clip of FIG. 9 rotated downward.
Figure 12:
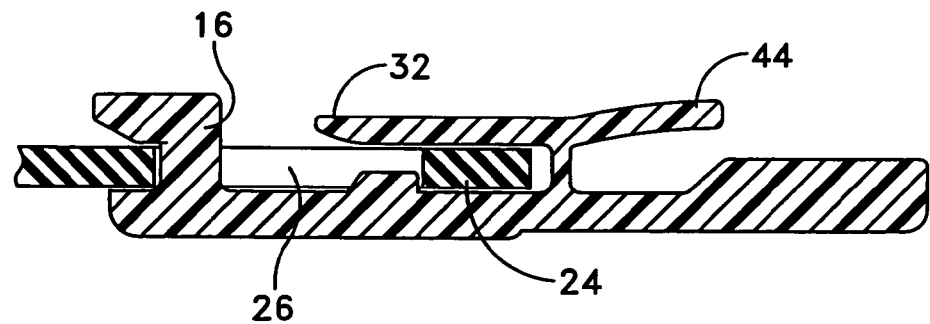
FIG. 12 is a cross sectional view taken along lines 12—12 of FIG. 9.

Detent 16 is preferably sized and spaced from engagement member 18 such that, when the stop enters opening 28, detent 16 engages inside surface 36 of opening 34. Detent 16 may preferably include a post 46 and a shoulder 48 that rides along the inside surface 36 during use. In order to rotate the clips 11, the user simply grasps the body portion and moves it either upward or downward (FIGS. 10 and 11). As the clip is moved in either the upward direction, arrow "B", (FIG. 10) or the downward direction, arrow "C", (FIG. 11), detent 16 rides on inside surface 36 of the opening 26.

Referring now to FIGS. 2 and 7–11, the goggle 10 includes opening 26 which is sized to receive both the detent 16 and one end of the engagement member 18. A first end 28 of the opening is sized to receive stop 30 disposed on an inner surface of clip 11 along with the inner end 32 of the engagement member (FIG. 7) as described above. In this manner, the clip is secured to the goggle in a similar manner that a clothes pin is secured to a clothes line. A second end 34 of the opening is sized such that detent 16 is able to ride on inside surface 36 of the opening in order to rotate the clips 11, as also described above. In the present embodiment, the first end 28 is generally circular and the second end 34 is generally rectangular, the first and second ends together forming opening 26. Alternately, the openings could have a variety of shapes, and could be formed as two, separate openings, or as an opening and a recess, as would be known to those of skill in the art.

It will be appreciated that the clip disclosed herein securely attaches a strap to eye wear, while also being easily adjustable and removable by the user.

It will be further understood that various modifications may be made to the embodiments disclosed herein. For example, the sizes and shapes disclosed herein may be readily varied, as would be known to those of skill in the art. In addition, the goggle may vary from the exemplary embodiment and may be any form of eye wear. Therefore, the above description should not be construed as limiting, but merely as exemplifications of preferred embodiments. Those skilled in the art will envision other modifications within the scope, spirit and intent of the invention.

What is claimed is:

1. A clip for removably attaching a strap to eye wear comprising:

a body portion including a front and a rear;

a slot disposed through the rear of the body portion and sized to receive an end of the strap;

a detent supported on an inner surface of the front of the body portion, opposite the slot, and including a post and a shoulder, the shoulder being constructed and arranged to ride along an inside surface disposed in a side portion of the eye wear so as to pivot the clip;

an engagement member pivotally supported on the inner surface of the body portion, between the slot and the detent, the engagement member including a lever having an inner end engageable with an opening disposed in the side portion of the eye wear, an outer end opposite the inner end, and a post there between such that the lever is pivotal on the post; and wherein the engagement member is adapted to engage the opening in the side portion of the eye wear, and whereby to disengage the clip the lever is pivoted such that the inner end is released from engagement with the opening.

2. The clip of claim 1, wherein the body portion, detent and engagement member are formed as a unitary member.

3. The clip of claim 1, further including a stop supported on the inner surface of the body portion, opposite the inner end of the engagement member.

4. The clip of claim 3, wherein the stop is sized to fit within the opening such that a portion of the side portion of the eye wear is sandwiched between inner surface of the body portion and the lever of the engagement member.

5. The clip of claim 1, wherein the shoulder of the detent is adapted to ride along the inside surface of the opening disposed in the side portion of the eye wear.

6. In combination, eye wear including a side portion, and a clip removably secured to the eye wear for attaching a strap to the eye wear, the combination comprising:

at least one opening disposed through the side portion of the eye wear;

a slot disposed through a rear of a body portion of the clip and sized to receive an end of the strap;

a detent supported on an inner surface of the front of the body portion, opposite the slot and including a post and a shoulder, the shoulder being constructed and arranged to ride along an inside surface disposed in the side portion of the eye wear so as to pivot the clip;

an engagement member pivotally supported on the inner surface of the body portion, between the slot and the detent, the engagement member including a lever having an inner end engageable with the at least one opening, an outer end opposite the inner end, and a post there between such that the lever is pivotal on the post; and wherein upon the engagement member entering the opening in the side portion of the eye wear, the shoulder of the detent engages the inside surface in the side portion of the eye wear, and whereby to disengage the clip the lever is pivoted such that the inner end is released from engagement with the opening.

7. The combination of claim 6, wherein the eye wear is a goggle.

8. The combination of claim 6, wherein the body portion, detent and engagement member are formed as a unitary member.

9. The combination of claim 6, further including a stop supported on the inner surface of the body portion, opposite the inner end of the engagement member.

10. The combination of claim 9, wherein the stop is sized to fit within the opening such that a portion of the side portion of the eye wear is sandwiched between inner surface of the body portion and the lever of the engagement member.

11. The combination of claim 6, further comprising a ramp disposed on the side portion of the eye wear and constructed and arranged to guide the engagement member into the opening.

12. The combination of claim 6, wherein the at least on opening comprises a first opening sized to receive the inner end of the lever and a second opening defining the inside surface which the detent rides along during pivoting.

* * * * *